United States Patent
Sugiyama (10) Patent No.: US 9,492,122 B2
(45) Date of Patent: Nov. 15, 2016

(54) MEDICAL IMAGE PROCESSING APPARATUS

(75) Inventor: Shinya Sugiyama, Nasushiobara (JP)

(73) Assignees: KABUSHIKI KAISHA TOSHIBA, Tokyo (JP); TOSHIBA MEDICAL SYSTEMS CORPORATION, Otawara-shi (JP)

(*) Notice: Subject to any disclaimer, the term of this patent is extended or adjusted under 35 U.S.C. 154(b) by 511 days.

(21) Appl. No.: 13/533,166

(22) Filed: Jun. 26, 2012

(65) Prior Publication Data

US 2013/0002657 A1 Jan. 3, 2013

(30) Foreign Application Priority Data

Jun. 28, 2011 (JP) ................. P2011-143476

(51) Int. Cl.
*G06F 3/048* (2013.01)
*A61B 6/02* (2006.01)
(Continued)

(52) U.S. Cl.
CPC .......... *A61B 6/02* (2013.01); *A61B 6/463* (2013.01); *A61B 6/466* (2013.01); *A61B 6/467* (2013.01); *A61B 6/469* (2013.01); *A61B 6/503* (2013.01);
(Continued)

(58) Field of Classification Search
CPC ....... G06T 15/00; G06T 17/00; G06T 15/20; G06F 3/048; H04N 13/0203
USPC ......................... 345/419; 600/407
See application file for complete search history.

(56) References Cited

U.S. PATENT DOCUMENTS 5,682,437 A * 10/1997 Okino et al. .............. 382/100
2004/0145585 A1 7/2004 Fontius
(Continued)

FOREIGN PATENT DOCUMENTS

CN 1517852 A 8/2004
CN 101653381 2/2010
(Continued)

OTHER PUBLICATIONS

Studholme, Colin, Derek LG Hill, and David J. Hawkes. "An overlap invariant entropy measure of 3D medical image alignment." Pattern recognition 32.1 (1999): 71-86.*

(Continued)

*Primary Examiner* — Ke Xiao
*Assistant Examiner* — Whitney Pointe
(74) *Attorney, Agent, or Firm* — Oblon, McClelland, Maier & Neustadt, L.L.P.

(57) ABSTRACT

According to one embodiment, a medical image processing apparatus includes an image obtaining unit, a three-dimensional medical image generating unit, a correction information obtaining unit, a display angle correcting unit, and a display unit. The image obtaining unit obtains medical image data including an object. The three-dimensional medical image generating unit generates stereoscopic three-dimensional medical image data including a plurality of objects based on the medical image data obtained by the image obtaining unit. The correction information obtaining unit obtains correction information for the plurality of objects. The display angle correcting unit corrects, based on the correction information, the three-dimensional medical image data so that a display angle of at least one of the plurality of objects is corrected. The display unit displays a three-dimensional medical image based on the three-dimensional medical image data corrected by the display angle correcting unit.

7 Claims, 11 Drawing Sheets

(51) Int. Cl.
*A61B 6/00* (2006.01)
*H04N 13/00* (2006.01)
*G06F 19/00* (2011.01)
*H04N 13/04* (2006.01)

(52) U.S. Cl.
CPC .......... *A61B 6/5217* (2013.01); *A61B 6/5223* (2013.01); *H04N 13/0014* (2013.01); *H04N 13/0468* (2013.01); *H04N 13/0472* (2013.01); *G06F 19/321* (2013.01); *H04N 13/0452* (2013.01)

(56) References Cited

U.S. PATENT DOCUMENTS

| | | | |
|---|---|---|---|
| 2004/0233193 A1* | 11/2004 | Margadant | 345/419 |
| 2005/0219240 A1* | 10/2005 | Vesely et al. | 345/419 |
| 2005/0264558 A1 | 12/2005 | Vesely et al. | |
| 2005/0264559 A1 | 12/2005 | Vesely et al. | |
| 2005/0264857 A1 | 12/2005 | Vesely et al. | |
| 2005/0264858 A1 | 12/2005 | Vesely et al. | |
| 2005/0275913 A1 | 12/2005 | Vesely et al. | |
| 2005/0275914 A1 | 12/2005 | Vesely et al. | |
| 2005/0275915 A1 | 12/2005 | Vesely et al. | |
| 2005/0281411 A1 | 12/2005 | Vesely et al. | |
| 2006/0007246 A1 | 1/2006 | Ackermann et al. | |
| 2006/0119622 A1 | 6/2006 | Kariathungal et al. | |
| 2007/0032720 A1* | 2/2007 | Koivukangas et al. | 600/407 |
| 2008/0095414 A1* | 4/2008 | Desh et al. | 382/128 |
| 2009/0147073 A1 | 6/2009 | Getty | |
| 2009/0147074 A1 | 6/2009 | Getty | |
| 2010/0040200 A1 | 2/2010 | Ema et al. | |
| 2011/0107270 A1 | 5/2011 | Wang et al. | |

FOREIGN PATENT DOCUMENTS

| | | |
|---|---|---|
| EP | 2 157 546 A2 | 2/2010 |
| JP | 2006-142021 | 6/2006 |
| JP | 2010-167129 | 8/2010 |

OTHER PUBLICATIONS

Extended European Search Report Issued Mar. 14, 2013 in Patent Application No. 12174171.4.

Roger J. Hubbold et al., "Stereoscopic Volume Rendering", CiteSeerX Beta Visualisation in Scientific Computing 98, XP002685946, 1998, 11 pages.

Combined Chinese Office Action and Search Report issued Mar. 5, 2014, in Chinese Patent Application No. 201210218466.X with English translation of category of cited documents.

Office Action issued Mar. 31, 2015, in Japanese Patent Application No. 2011-143476, filed Jun. 28, 2011.

Office Action issued Jan. 6, 2015, in Chinese Patent Application No. 201210218466.

Office Action issued Aug. 18, 2015, in Chinese Patent Application No. 201210218466.X.

* cited by examiner

MEDICAL IMAGE PROCESSING APPARATUS

CROSS-REFERENCE TO RELATED APPLICATIONS

This application claims the benefit of priority of Japanese Patent Application No. 2011-143476, filed Jun. 28, 2011, the entire contents of which are incorporated herein by reference.

FIELD

Embodiments described herein relate generally to a medical image processing apparatus.

BACKGROUND

A volume rendering (VR) technique is known. In the VR technique, a medical image taken by a diagnostic imaging apparatus is reconstructed into volume image data, and then the resultant data is displayed on a monitor as a 2D image. To provide the volume image with a realistic sense of depth, it is also considered to display such an image in three dimensions. Three-dimensional display of medical images is expected to be applied in a variety of situations such as a preoperative conference, an operative planning simulation, and intraoperative navigation.

It is known that a 3D image is given in a stereoscopic view by typically using glasses for stereopsis, but recently, glasses-free 3D monitors have been developed that provide stereoscopic views without special glasses. If the glasses-free 3D monitors are applied in a medical field, for example, stereoscopic images can be utilized without bothersome glasses also in operation.

Also, in operation, since multiple persons may stereoscopically view a medical image simultaneously from different directions through a glasses-free 3D monitor, technology has been developed that enables stereopsis even if a glasses-free 3D monitor is viewed from every angle.

If a single object is stereoscopically viewed on a glasses-free 3D monitor, two or more multi-parallax images are displayed with different directivities. Thereby, the object can be stereoscopically viewed from multiple directions as well as from the front.

In medical practice, images of a plurality of objects may be displayed to make a comparative review of specific sites of the objects. In order to make a proper comparative review when a plurality of objects is stereoscopically viewed on a single screen, display of such objects has been considered in many ways. For example, there is a method for creating parallax images based on one focus in one virtual space including a plurality of objects.

However, if parallax images are created based on one focus in a virtual space including a plurality of objects, for the stereoscopic objects, a side facing a viewer from the focus and a side opposite thereto (inner sides of the objects) are viewed. Thus, each object is not displayed at a same side and a same angle, so that it is challenging for the viewer to make a comparative review.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of a medical image processing apparatus according to embodiments of the present invention with reference to the drawings.

In general, according to one embodiment, a medical image processing apparatus includes an image obtaining unit, a three-dimensional medical image generating unit, a correction information obtaining unit, a display angle correcting unit, and a display unit. The image obtaining unit obtains medical image data including an object. The three-dimensional medical image generating unit generates stereoscopic three-dimensional medical image data including a plurality of objects based on the medical image data obtained by the image obtaining unit. The correction information obtaining unit obtains correction information for the plurality of objects. The display angle correcting unit corrects, based on the correction information, the three-dimensional medical image data so that a display angle of at least one of the plurality of objects is corrected. The display unit displays a three-dimensional medical image based on the three-dimensional medical image data corrected by the display angle correcting unit.

Figure 1:
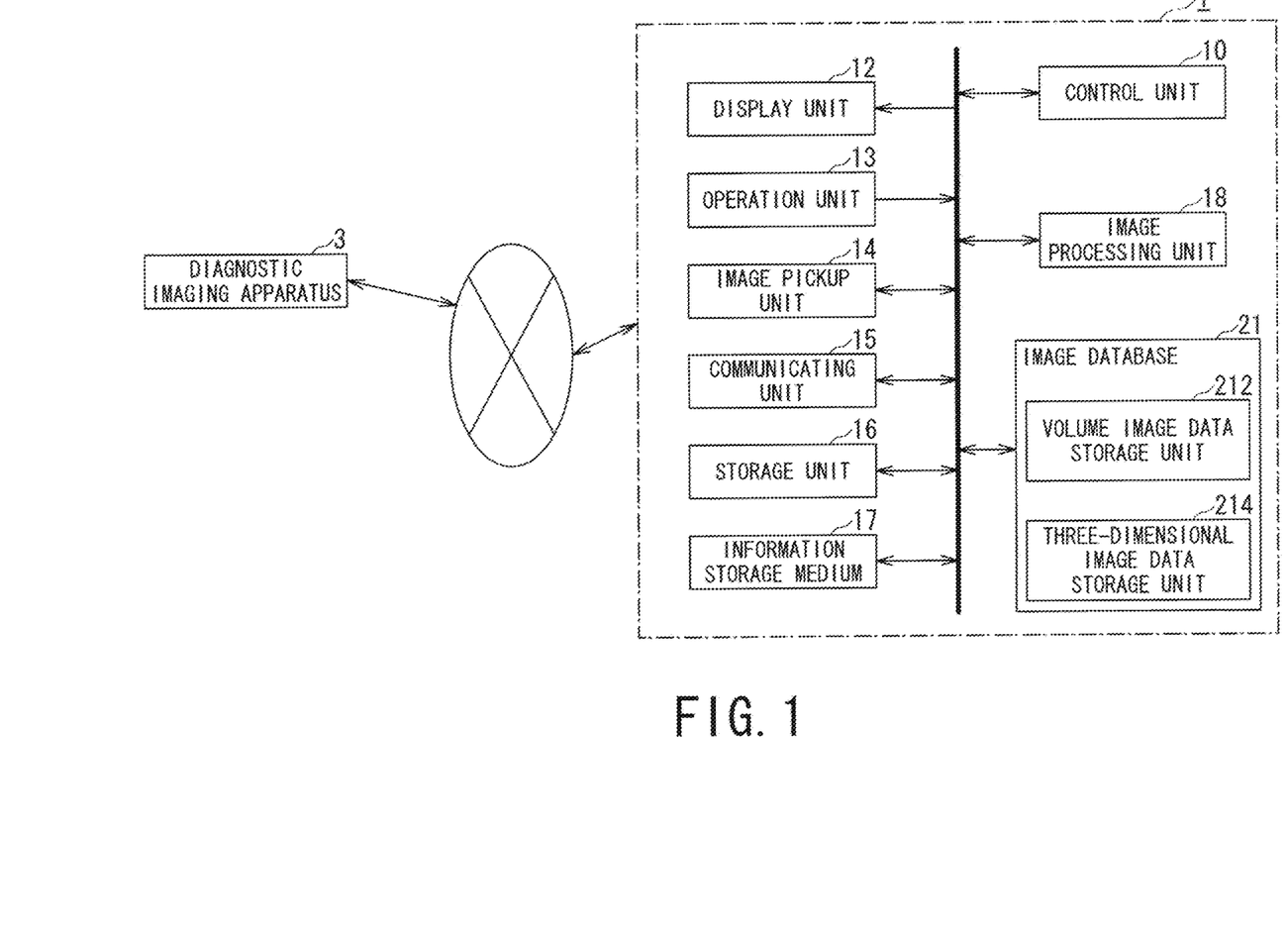
FIG. 1 is a block diagram illustrating a medical image processing apparatus according to an embodiment of the present invention, which is a network system with a diagnostic imaging apparatus.

FIG. 1 is a block diagram illustrating a medical image processing apparatus 1 according to an embodiment of the present invention, which is a network system with a diagnostic imaging apparatus 3. The medical image processing apparatus 1 is connected with another apparatus such as the diagnostic imaging apparatus 3 via a LAN in a hospital so that they can communicate with each other.

The diagnostic imaging apparatus 3 is a modality such as an X-ray CT apparatus. The diagnostic imaging apparatus 3 X-rays a subject and has medical image data.

The medical image processing apparatus 1 includes a control unit 10, a display unit 12, an operation unit 13, an image pickup unit 14, a communicating unit 15, a storage unit 16, an information storage medium 17, an image processing unit 18, and an image database 21, which are connected with each other via a bus so that they can communicate with each other.

The operation unit 13 is an input device such as a touch panel, an operation key, and a mouse. The operation unit 13 changes a display orientation (a display angle) of at least one object in a medical image displayed on the display unit 12. The display unit 12 is a monitor or the like and displays at least a three-dimensional medical image. The communicating unit 15 is connected to a hospital LAN and communicates with the diagnostic imaging apparatus 3.

The image pickup unit 14 is a device that senses an orientation of an operator. Details thereof will be described later.

The image database 21 includes a volume image data storage unit 212 and a three-dimensional image data storage unit 214. The volume image data storage unit 212 stores volume image data obtained by the diagnostic imaging apparatus 3 picking up an image and an image processing circuit 182 in the image processing unit 18 processing the image. The volume image data is used as original data of a volume image to be displayed on the display unit 12. The three-dimensional image data storage unit 214 stores multiple items of parallax image data generated by a three-dimensional image generating unit 183 based on the volume image data. Each of the multiple items of parallax image data is used as original data of a parallax image. A plurality of parallax images are each displayed in predetermined parallax from the display unit 12, so that the images are perceived by the operator as stereoscopic three-dimensional medical images. Hereinafter, the multiple items of parallax image data are collectively referred to as the (stereoscopic) three-dimensional medical image data, and the plurality of parallax images are collectively referred to as the three-dimensional medical images. The three-dimensional medical image data is used as original data of three-dimensional medical images. Details thereof will be described later.

Figure 2:
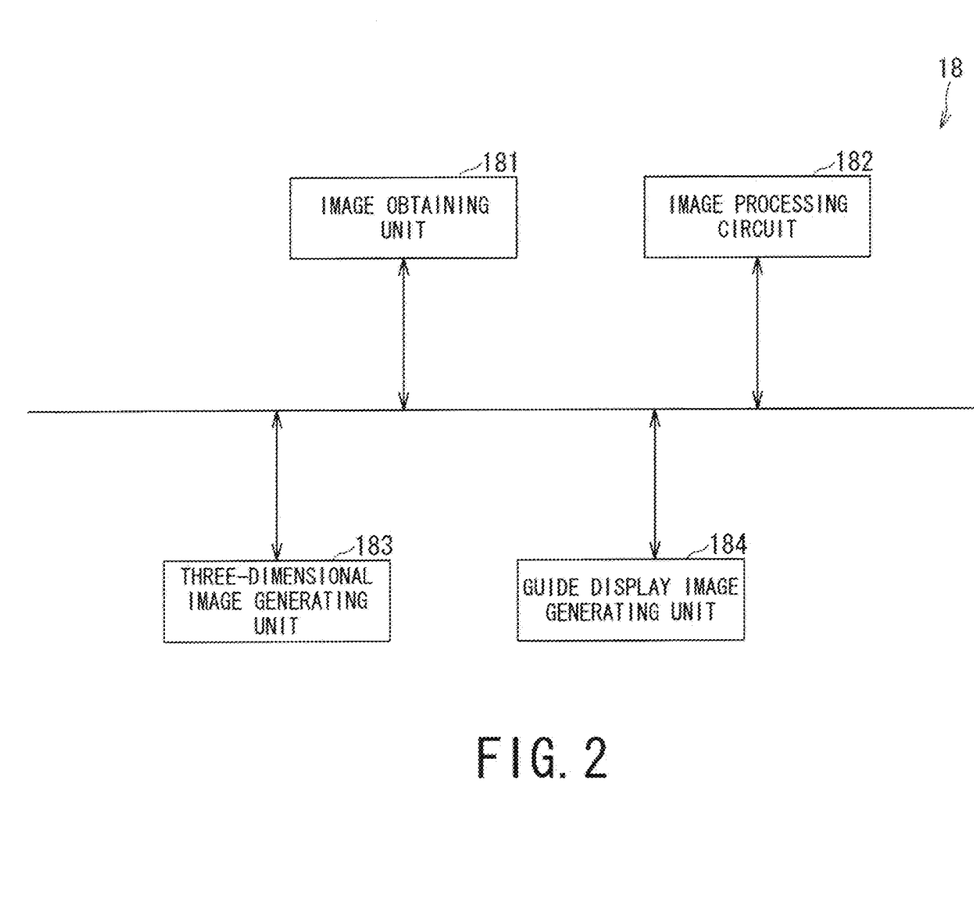
FIG. 2 is a block diagram illustrating details of an image processing unit.

The image processing unit 18 performs various types of processing on image data. FIG. 2 illustrates details of the image processing unit 18. The image processing unit 18 includes an image obtaining unit 181, the image processing circuit 182, the three-dimensional image generating unit 183, and a guide display image generating unit 184.

The image obtaining unit 181 obtains image data picked up by the diagnostic imaging apparatus 3. The image processing circuit 182 performs image processing on the image data obtained by the image obtaining unit 181 to create volume image data. The three-dimensional image generating unit 183 generates, based on the volume image data processed by the image processing circuit 182, nine items of parallax image data (three-dimensional medical image data) that are, for example, original data of nine parallax images of a same site viewed from different angles. As a result, the display unit 12 can display stereoscopic three-dimensional medical images.

Also, the three-dimensional image generating unit 183 generates, based on other image data obtained by the image obtaining unit 181, three-dimensional medical image data in the same manner to generate multiple items of three-dimensional medical image data. The three-dimensional image generating unit 183 then causes the display unit 12 to display three-dimensional medical images based on a predetermined number of items of the plurality of items of the three-dimensional medical image data.

Further, the three-dimensional image generating unit 183 arranges the plurality of items of three-dimensional medical image data in a same projection space in response to an instruction from an object selecting unit 101. Also, the three-dimensional image generating unit 183 changes the relative arrangement of the plurality of items of three-dimensional medical image data in the same projection space in response to an instruction from the object selecting unit 101.

Based on an angle calculated by a display angle correcting unit 107 in the control unit 10, the guide display image generating unit 184 generates a guide such as an arrow to be displayed on the display unit 12 for the operator to view a three-dimensional medical image from a proper angle.

A storage unit 16 is a work area for the control unit 10, the communicating unit 15, etc. and may be RAM (Random Access Memory) or the like.

The information storage medium 17 (computer-readable medium) is used for storing a program and data, and may be a hard disk drive, memory (Flash Memory, ROM: Read Only Memory), or the like. In the information storage medium 17, a program for causing a computer to function as each component in the embodiments described herein (a program for causing the computer to perform processing of each component), and a plurality of applications for displaying three-dimensional medical images are stored.

The control unit 10 is a calculating device for controlling the entire medical image processing apparatus 1 and performing other various types of arithmetic and control processing. The functions of the control unit 10 may be achieved by hardware such as various processors (a CPU, a DSP, etc.) and ASIC (a gate array etc.), and by programs. The control unit 10 performs a variety of processes of the present embodiment based on the programs (data) stored in the information storage medium 17.

Figure 3:
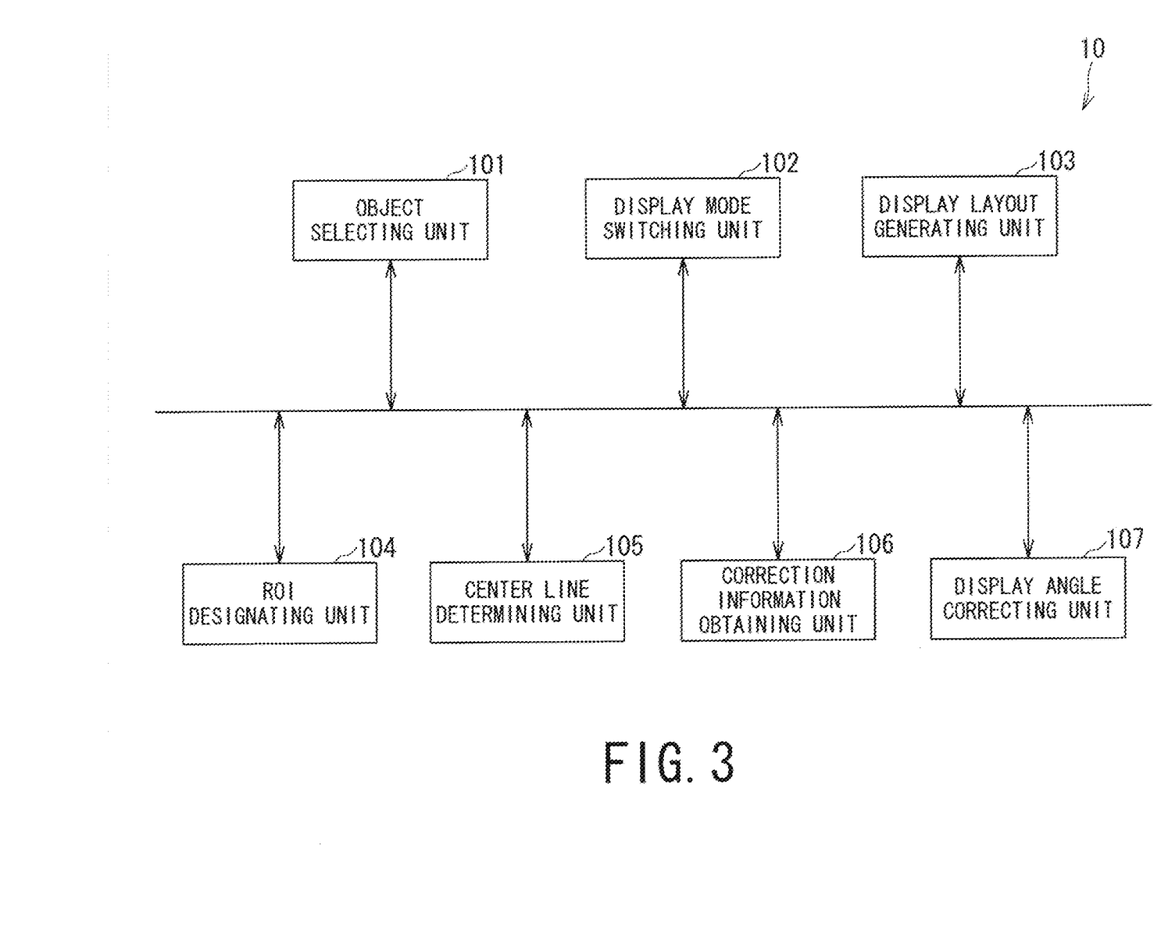
FIG. 3 is a block diagram illustrating details of a control unit.

FIG. 3 is a block diagram illustrating details of the control unit 10. The control unit 10 includes the object selecting unit 101, a display mode switching unit 102, a display layout generating unit 103, an ROI designating unit 104, a center line determining unit 105, a correction information obtaining unit 106, and the display angle correcting unit 107.

The object selecting unit 101 selects objects to be compared from a plurality of three-dimensional medical images (objects) based on the items of three-dimensional medical image data generated by the three-dimensional image generating unit 183. The object selecting unit 101 may select objects in response to an instruction given by the operator through the operation unit 13, or may automatically select objects that meet one of predetermined selection criteria. Also, the object selecting unit 101 may select a plurality of two-dimensional medical images (objects) from two-dimensional medical images based on the image data obtained by the image obtaining unit 181. In this case, the three-dimensional image generating unit 183 generates three-dimensional medical image data for each of the image data items selected by the object selecting unit 101 and arrange the generated data in a same projection space.

The selection criteria are classified, for example, as the following types: one for selecting objects in a same space; another for selecting objects of a same site with only performed image processing being different; and yet another for selecting objects of a same site with only image obtaining times being different.

The objects in a same space refer to objects of, for example, a same site or an internal organ, or objects with positions of at least one of x, y, and z axes being the same.

The objects of a same site with only performed image processing being different refer to, for example, objects of a same site with only the absence or presence of bone display being different, objects of a same site with only the absence or presence of internal organ display being different, objects of a differential image and an original image, or objects of a same site with rendering processing being different.

The objects of a same site with only image obtaining times being different refer to an object of a latest image obtained by the diagnostic imaging apparatus 3 and an object of a previous image, objects seen before and after injecting a contrast medium agent, or the like.

The display layout generating unit 103 generates a layout in which a plurality of objects selected by the object selecting unit 101 is vertically arranged.

The display mode switching unit 102 switches from a volume image displayed on the display unit 12 to a stereoscopic three-dimensional medical image.

The ROI designating unit 104 designates an image region from the stereoscopic three-dimensional medical image switched by the display mode switching unit 102.

The center line determining unit 105 calculates a center line in the image region designated by the ROI designating unit 104.

The correction information obtaining unit 106 obtains correction information from external devices such as the operation unit 13 and the image pickup unit 14. For example, the correction information obtaining unit 106 obtains from the operation unit 13 the absence or presence of change in a display angle of an object and an amount of the angle change of the object. Also, the correction information obtaining unit 106 obtains from the image pickup unit 14 the absence or presence of change in a display angle of an object based on a sensed orientation of the operator and an amount of the angle change of the object.

The display angle correcting unit 107 calculates a correction angle based on the correction information obtained by the correction information obtaining unit 106.

Next, the operation of the medical image processing system with this structure will be described.

First Embodiment

As a first embodiment, an exemplary operation for vertically arranging a plurality of compared objects to be stereoscopically viewed will be described with reference to FIG. 4.

First, the image obtaining unit 181 in the control unit 10 obtains image data including a plurality of objects from the diagnostic imaging apparatus 3 (step S101). Then, image processing is performed by the image processing circuit 182 to create two-dimensional volume image data, which is stored in the volume image data storage unit 212 and displayed on the display unit 12 (step S103).

Next, the object selecting unit 101 selects a plurality of objects to be stereoscopically viewed from the volume image data created and stored in the volume image data storage unit 212 in step S103 (step S105). The objects may be manually selected by an operator giving an instruction through the operation unit 13, or objects that meet one of predetermined selection criteria such as mentioned above may be automatically selected.

After the objects are selected in step S105, when the operator switches a display mode through the operation unit 13, the display mode switching unit 102 makes an instruction to switch from two-dimensional display, which is in a normal mode, to three-dimensional display, which is in a stereoscopic view mode (step S107). In response to the display switching in step S107, the three-dimensional image generating unit 183 generates, from the volume image data stored in the volume image data storage unit 212 in step S103, for example, nine items of parallax image data (stereoscopic three-dimensional medical image data) that is original data of nine parallax images and stores the generated data in the three-dimensional image data storage unit 214 (step S109).

Next, the display layout generating unit 103 generates a layout for the display unit 12 so as to vertically arrange the objects selected in step S105, of the stereoscopic three-dimensional medical image data stored in the three-dimensional image data storage unit 214 in step S109 (step S111). The display unit 12 vertically arranges and displays the selected objects based on the layout generated in step S111 (step S113).

In this manner, if a plurality of objects is compared to each other in stereoscopic vision, displaying vertically arranged objects enables observing each object from a same side and a same angle.

Figure 5A:
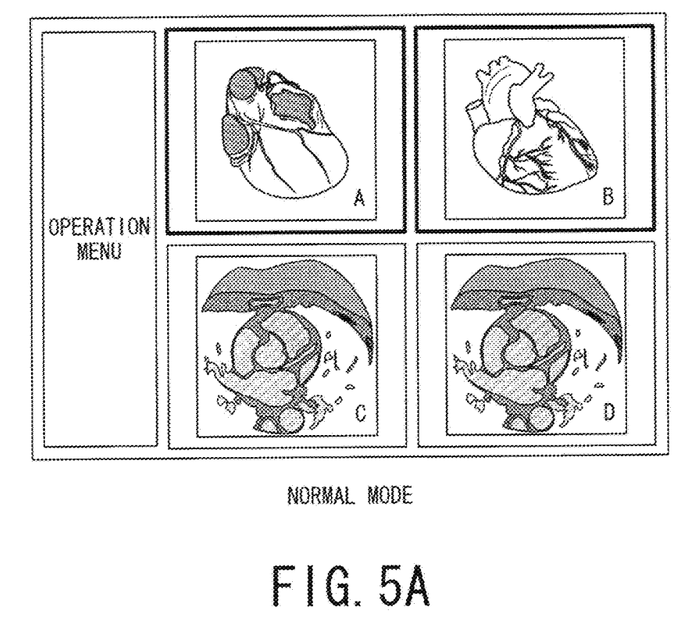
FIG. 5A shows a display example in a normal mode whereby arrangement of a plurality of compared objects is to be changed into vertical.
Figure 5B:
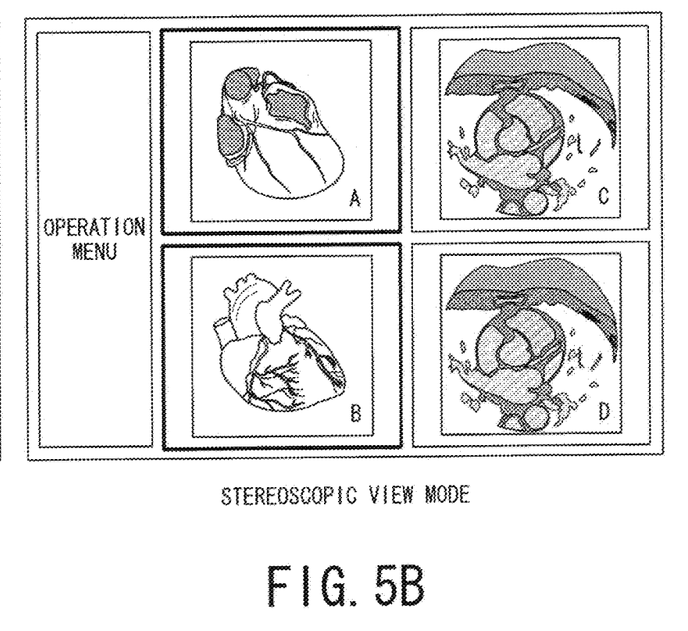
FIG. 5B shows a display example in a stereoscopic view mode whereby the arrangement of the plurality of compared objects has been changed into vertical.

Display examples on the display unit 12 are shown in FIGS. 5A and 5B. FIG. 5A shows a normal mode, and FIG. 5B shows a stereoscopic view mode. In the normal mode (two-dimensional display) shown in FIG. 5A, if an image A and an image B are selected, the selected objects are indicated with solid frames. At this time, the image A and the image B are arranged horizontally in row. When the display mode switching unit 102 switches from the normal mode to the stereoscopic view mode, the image A and the image B are rearranged vertically and three-dimensionally displayed. An image C and image D, which are not selected, are displayed in a blank area other than areas where the image A and the image B are displayed.

Variation of First Embodiment

Figure 6:
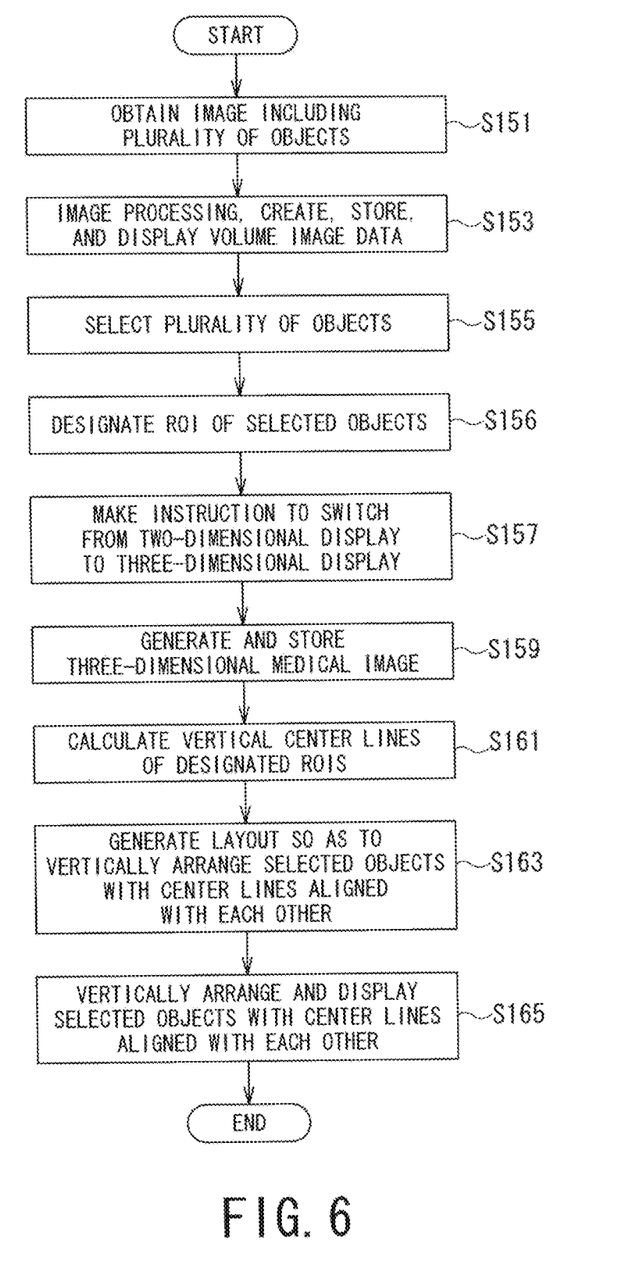
FIG. 6 is a flow chart showing the operation for, if display sizes of a plurality of compared objects are different, designating a region to be compared of each object.

As a variation of the first embodiment, the operation of designating a region of each object, to be compared will be described with reference to FIG. 6. This is the case in which the display sizes of a plurality of compared objects selected by the object selecting unit 101 are different from each other.

Figure 4:
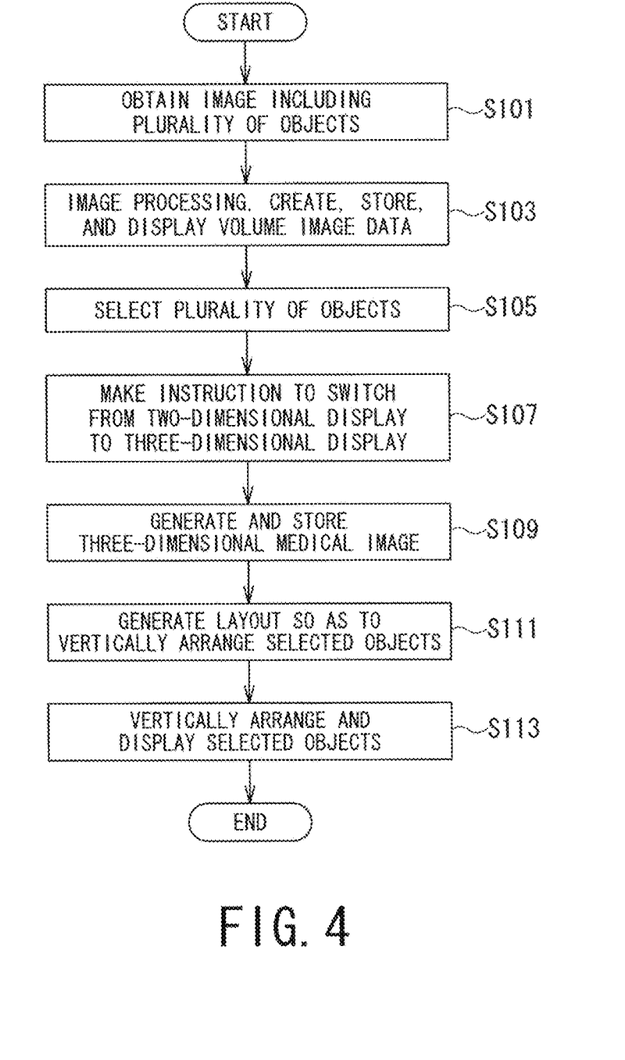
FIG. 4 is a flow chart showing the operation for vertically arranging a plurality of compared objects to be displayed for stereopsis.

Since steps S151 to S155 are the same as steps S101 to S105 in FIG. 4, descriptions thereof will be omitted.

Thereafter, the ROI designating unit 104 designates each region (ROI) to be compared of the plurality of objects selected by the object selecting unit 101 in step S155 (step S156). Such regions may be manually designated by an operator giving an instruction through the operation unit 13, or predetermined regions may be automatically designated. Also, if there is no specific designation, the entire regions may be designated as ROIs.

After the regions of the objects are designated in step S156, when the operator changes a display mode through the operation unit 13, the display mode switching unit 102 makes an instruction to switch from two-dimensional display, which is in a normal mode, to three-dimensional display, which is in a stereoscopic view mode (step S157). In response to the display mode switching in step S157, the three-dimensional image generating unit 183 generates, from the volume image data stored in the volume image data storage unit 212 in step S153, for example, nine items of parallax image data (stereoscopic three-dimensional medical image data) that is original data of nine parallax images and stores the generated data in the three-dimensional image data storage unit 214 (step S159).

Next, the center line determining unit 105 calculates a vertical center line of each object's ROI designated in step S156 (step S161).

Then, the display layout generating unit 103 generates a layout for the display unit 12 (step S163). In the layout, the plurality of objects selected by the object selecting unit 101 are vertically aligned with each other along the vertical center line of each object determined by the center line determining unit 105 in step S161. The display unit 12 displays the selected objects vertically aligned along with each other along the center line based on the layout generated in step S163 (step S165).

In this manner, if a plurality of objects with different display sizes is compared to each other in stereoscopic vision, displaying objects aligned along a vertical center line enables observing each object from a same side and a same angle. It should be noted that when a layout is generated in step S163, the display size of at least one of selected objects may be reduced in order that the objects can be arranged in vertical display areas.

Figure 7A:
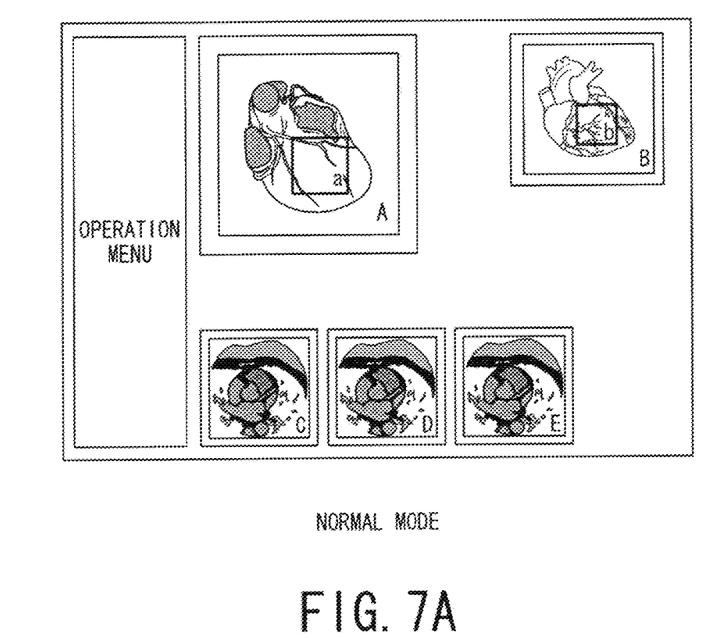
FIG. 7A shows a display example in a normal mode in the case where a plurality of compared objects are different in display size.
Figure 7B:
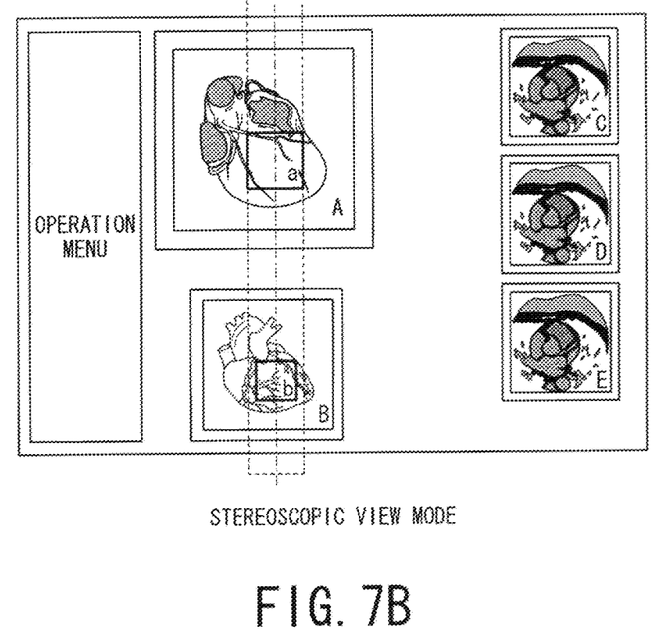
FIG. 7B shows a display example in a stereoscopic view mode in the case where the plurality of compared objects are different in display size.

Display examples on the display unit 12 are shown in FIGS. 7A and 7B. FIG. 7A shows a normal mode, and FIG. 7B shows a stereoscopic view mode. In the normal mode (two-dimensional display) shown in FIG. 7A, if regions in an image A and an image B are designated, a region "a" and region "b" of the selected objects are indicated with solid frames. At this time, the image A and the image B are different from each other in display size and are arranged horizontally in row. When the display mode switching unit 102 switches from the normal mode to the stereoscopic view mode, the image A and the image B are vertically aligned with each other along the center line of the region a and the region b, and three-dimensionally displayed.

Second Embodiment

Figure 8:
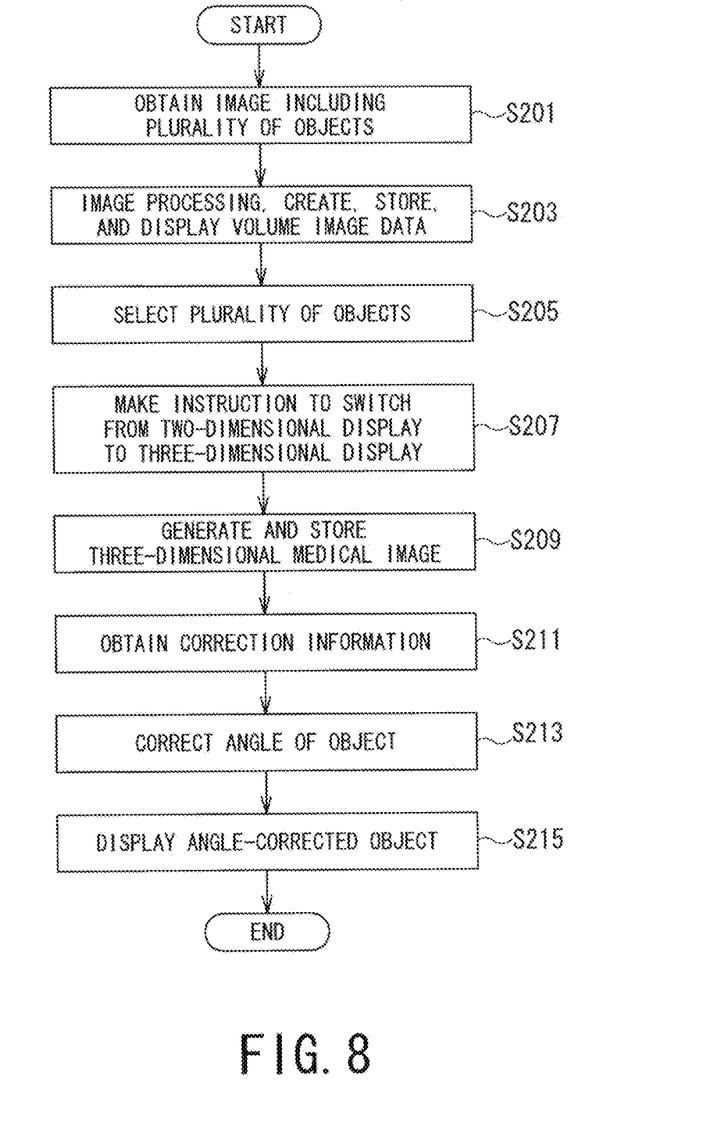
FIG. 8 is a flow chart showing the operation for correcting display angles of a plurality of compared objects to be stereoscopically viewed.

Next, as a second embodiment, an exemplary operation for correcting a display angle of a plurality of compared objects to be stereoscopically viewed is shown in FIG. 8.

Since steps S201 to S209 are the same as steps S101 to S109 in FIG. 4, descriptions thereof will be omitted.

Thereafter, the correction information obtaining unit 106 obtains correction information from the operation unit 13 and the image pickup unit 14 (step S211). The display angle correcting unit 107 then corrects, based on the correction information obtained in step S211, an angle of an appropriate object of the three-dimensional medical image data generated in step S209 (step S213). Then, the display unit 12 displays the object, the angle of which has been corrected (step S215).

The correction information obtained in step S211 indicates the absence or presence of change in an orientation of a displayed object (display angle) and an amount of the object's angle change. The information is used to cause a plurality of selected objects to face the operator (i.e., a direction in which a same side of each object can be observed by the operator). For example, this is information such as the absence or presence of change in a display angle of an object and an amount of the angle change, which is caused by an operation dial of the operation unit 13 being turned so as to face the operator. Alternately, for example, this is information such as the absence or presence of change in a display angle of an object and an amount of the object's angle change, which is based on the operator's orientation detected by the image pickup unit 14. The correction information may include an angle and a focal length.

Figure 9A:
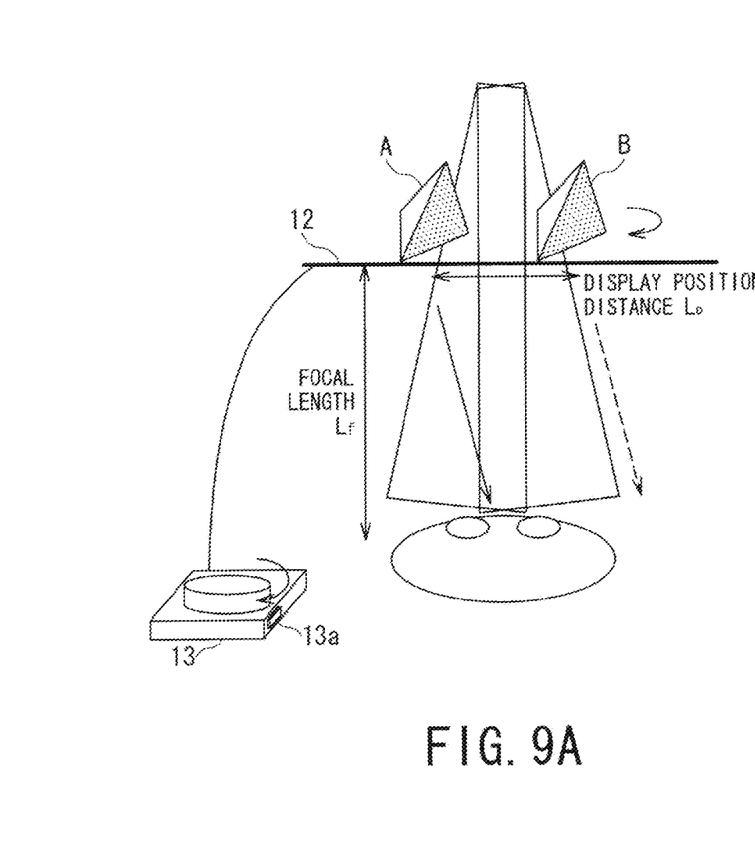
FIG. 9A is a concept diagram in which an object has not been rotated yet by an angle operation device.
Figure 9B:
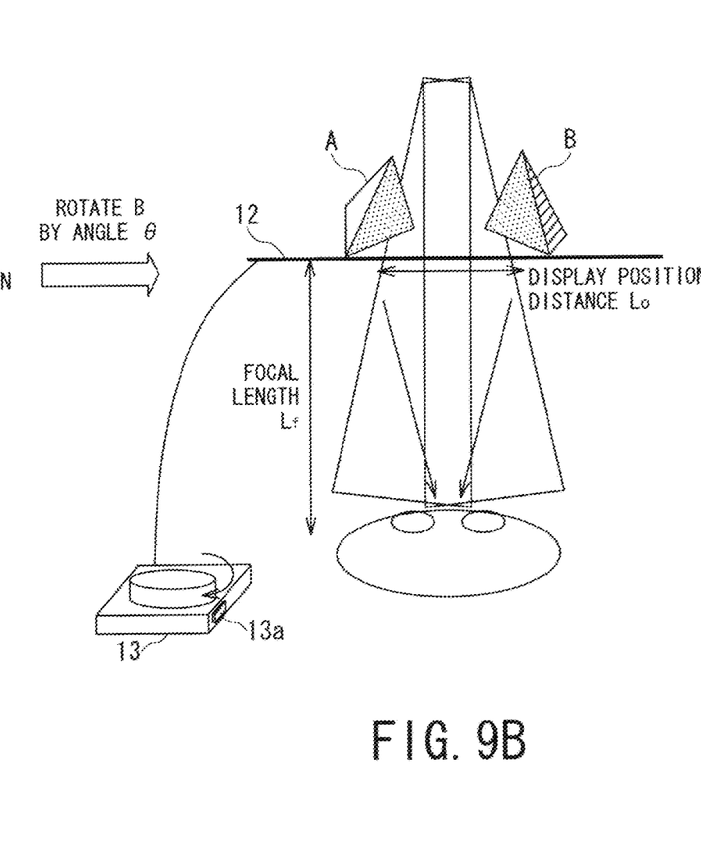
FIG. 9B is a concept diagram in which the object has been rotated by the angle operation device.

FIGS. 9A and 9B are concept diagrams illustrating the case in which if an operator faces objects, an object is rotated with the operation unit 13. The operator turns the operation dial of the operation unit 13 to rotate an object B from an orientation shown in FIG. 9A to an orientation shown in FIG. 9B so as to achieve an angle at which a same side can be observed from the operator. Thus, the display orientation of the object B is changed from an arrow direction of a dotted line shown in FIG. 9A to an arrow direction of a solid line shown in FIG. 9B.

The rotation angle θ of the object B is calculated based on a display position distance $L_o$ and a focal length $L_f$ from the operator to a display position.

Thus, in a stereoscopic view, since the same side of the objects A and B faces the operator, the operator can make a comparative observation of the object A and the object B for the same side.

It should be noted that regarding the operation unit 13 in FIG. 9, one of the objects (e.g., the object B) may be rotated by turning the operation dial with a button 13a being pressed, and both the objects A and B may be rotated by turning the operation dial without pressing the button 13a.

Figure 10A:
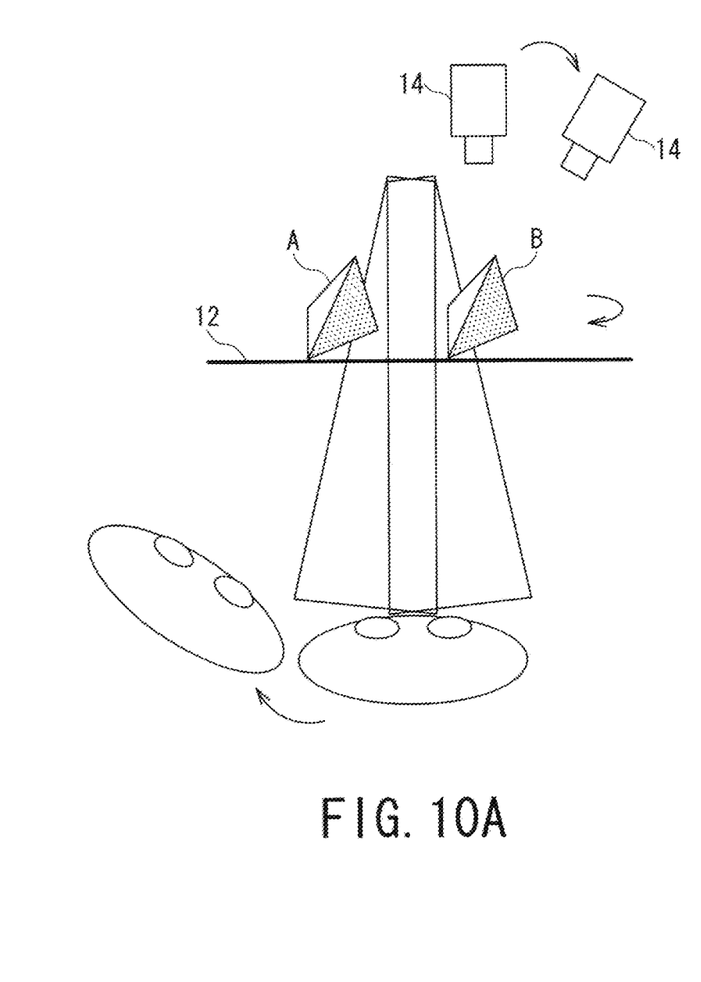
FIG. 10A is a concept diagram illustrating an example that an image pickup apparatus senses an angle of an operator to correct a display angle of objects in the case where the operator observes the objects from the front.
Figure 10B:
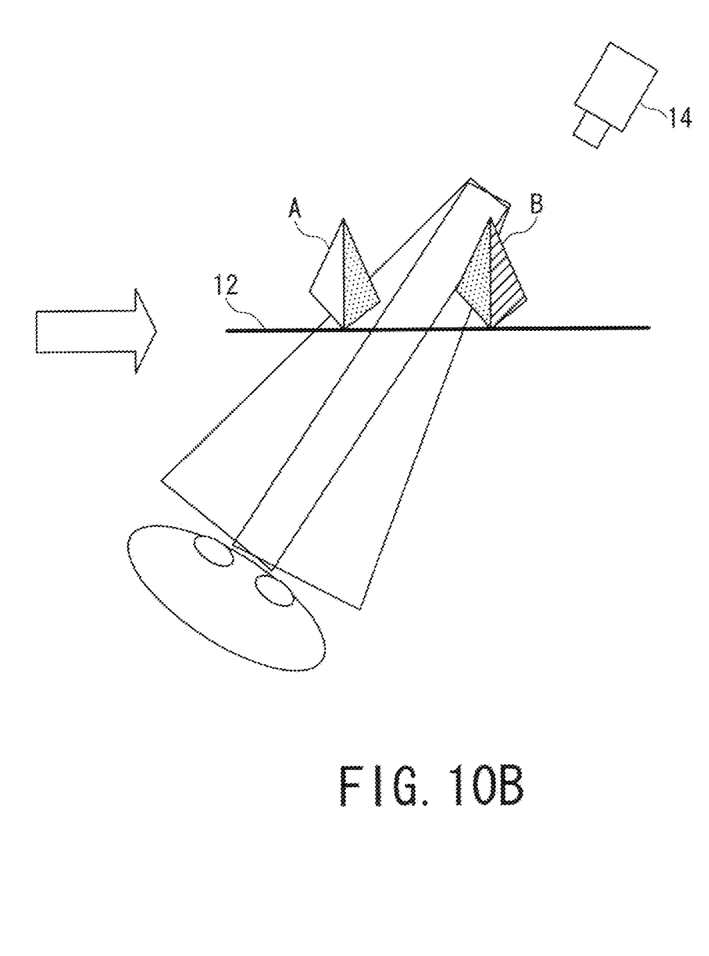
FIG. 10B is a concept diagram illustrating an example that the image pickup apparatus senses an angle of the operator to correct the display angle of the objects in the case where the operator observes the objects from any angle.

Also, the image pickup unit 14 may sense an angle of the operator with respect to the display unit 12 to correct a display angle of the object. Concept diagrams of this case are shown in FIGS. 10A and 10B. In FIG. 10A, if the operator viewing the display unit 12 from the front moves and now observes objects at any angle with the display unit 12, then the image pickup unit 14 senses the angle with the display unit 12 in accordance with the movement of the operator. Next, as shown in FIG. 10B, the image pickup unit 14 rotates the objects A and B so as to face the operator based on the sensed angle information.

Thereby, even if the operator does not view the display unit from the front, the operator can make a comparative observation of the same side of the objects A and B which are to be stereoscopically viewed, in the same manner as the case where the objects are seen from the front.

Variation of Second Embodiment

Also, a variation of the second embodiment will be described. In the variation, the display unit 12 may display a guide such as an arrow having a direction in which the operator can observe objects A and B face-to-face. A concept diagram of this case is shown in FIG. 11.

Figure 11:
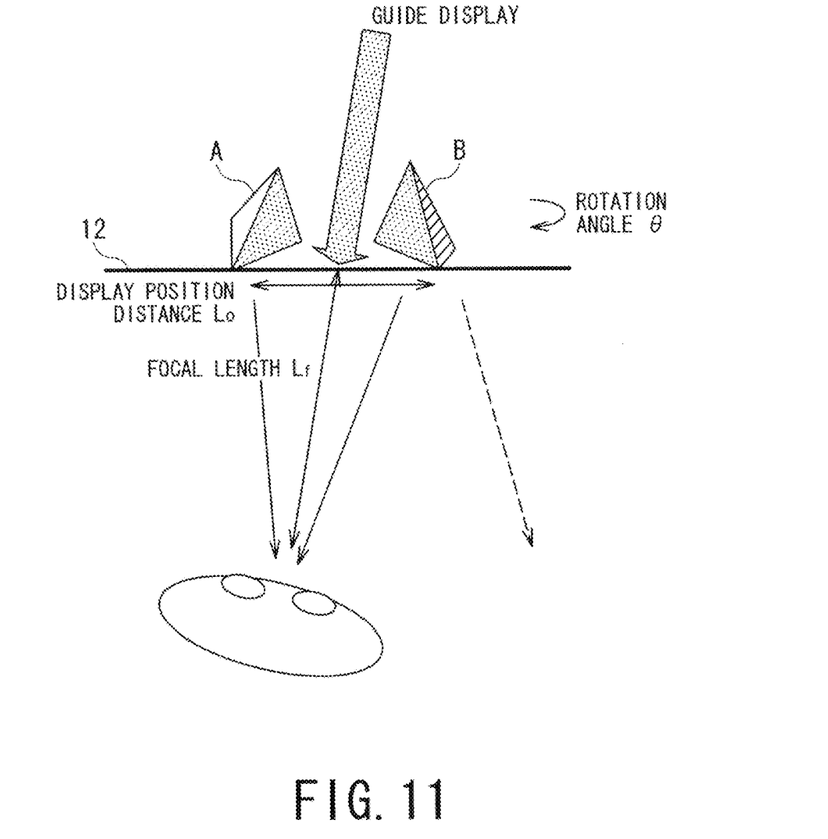
FIG. 11 is a concept diagram illustrating an example of guide display for the case in which the operator observes a rotated object face-to-face.

In FIG. 11, based on an angle of the objects A and B that is corrected by the display angle correcting unit 107 in step S215, the guide display image generating unit 184 in the image processing unit 18 generates an arrow indicating a direction in which the operator can observe the objects A and B face-to-face. The guide display image generating unit 184 then displays the arrow on the display unit 12 as guide display.

In FIG. 11, an angle φ of the guide display with the display unit 12 is calculated based on a rotation angle θ of the object B, a display position distance $L_o$, and a focal length $L_f$ from the operator to the display position.

Thus, presenting guide display to the operator in a stereoscopic view enables the operator to observe the objects face-to-face from an angle according to the guide display.

It is noted that the length of an arrow of guide display may indicate a focal length. Also, guide display may be displayed on a display device (another monitor, a rotatable device such as a Web camera, or the like) that is independent of the monitor for displaying objects.

According to the embodiments hereinbefore described, if a plurality of objects on the same screen is stereoscopically displayed, objects to be compared are vertically displayed. Alternatively, at least one of objects to be compared is rotated and displayed so that the operator views the objects face-to-face. These ways can achieve stereoscopic display of objects on the display unit so that a same side of the objects is seen from a same angle.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
an image obtaining unit configured to obtain medical image data including an object;
a three-dimensional medical image generating unit configured to arrange a plurality of objects in a same projection space based on the medical image data obtained by the image obtaining unit, and to generate stereoscopic three-dimensional medical image data including the plurality of objects in the same projection space;
a correction information obtaining unit configured to obtain correction information for the plurality of objects;
a display angle correcting unit configured to correct the three-dimensional medical image data so as to correct a display angle of at least one of the plurality of objects in the same projection space based on the correction information; and
a display unit configured to display a three-dimensional medical image based on the three-dimensional medical image data corrected by the display angle correcting unit, wherein
the three-dimensional medical image generating unit generates stereoscopic three-dimensional medical image data including the plurality of objects in the same projection space such that a plurality of objects are stereoscopically visible so that same faces of the plurality of objects are stereoscopically visible from a same angle of observation by an operator, and
the display angle correcting unit corrects the three-dimensional medical image data so as to correct the display angle of the plurality of objects in the same projection space based on the correction information such that the same faces of the plurality of objects are stereoscopically visible from the same angle of observation by the operator.

2. The medical image processing apparatus according to claim 1, wherein the correction information obtained by the correction information obtaining unit is an amount of change in a display angle of the plurality of objects such that the plurality of objects face an operator.

3. The medical image processing apparatus according to claim 1, wherein the correction information obtaining unit obtains the correction information from at least one of an angle operation device configured to rotate a display angle of the object and a detecting device configured to detect an orientation of an operator.

4. The medical image processing apparatus according to claim 1, further comprising a guide display angle calculating unit configured to calculate an angle for presenting guide display to an operator based on a display angle corrected by the display angle correcting unit,
wherein the display unit is configured to display a guide based on the angle calculated by the guide display angle calculating unit.

5. The medical image processing apparatus according to claim 1, wherein the plurality of objects are any of objects at least, objects in a same space, objects of a same site with only performed image processing being different, and objects of a same site with only obtaining times by the image obtaining unit being different.

6. The medical image processing apparatus according to claim 1, further comprising an object selecting unit configured to select the plurality of objects from the objects included in the medical image data obtained by the image obtaining unit,
wherein the display layout generating unit disposes an object that is not selected by the object selecting unit in a blank display area of the display unit.

7. The medical image processing apparatus according to claim 1, further comprising:
an image processing unit configured to perform image processing on the medical image data obtained by the image obtaining unit to generate volume image data including the plurality of objects; and
a display mode switching unit configured to make an instruction to switch a type of an image displayed on the display unit from the volume image generated by the image processing unit to the three-dimensional medical image,
wherein the display angle correcting unit corrects the three-dimensional medical image data so as to correct the display angle of at least one of the plurality of objects in the same projection space based on the correction information when the display mode switching unit makes the instruction.

* * * * *